United States Patent [19]

Lohse et al.

[11] Patent Number: 4,537,946
[45] Date of Patent: Aug. 27, 1985

[54] CURABLE MIXTURES CONTAINING EPOXY RESINS AND ISOMELAMINES

[75] Inventors: Friedrich Lohse, Oberwil; Helmut Zondler, Bottmingen, both of Switzerland

[73] Assignee: Ciba-Geigy Corporation, Ardsley, N.Y.

[21] Appl. No.: 675,906

[22] Filed: Nov. 28, 1984

Related U.S. Application Data

[62] Division of Ser. No. 466,454, Feb. 15, 1983, Pat. No. 4,499,268.

[30] Foreign Application Priority Data

Feb. 23, 1982 [CH] Switzerland .......................... 1105/82

[51] Int. Cl.$^3$ ................................................ C08G 59/50
[52] U.S. Cl. .................................... 528/118; 525/504; 528/361; 528/407; 528/393
[58] Field of Search ............... 528/118, 361, 407, 393; 525/504

[56] References Cited

U.S. PATENT DOCUMENTS 4,393,181 7/1983 Allen ................................. 525/504
4,486,583 12/1984 Takahashi et al. ................. 528/422

Primary Examiner—Earl Nielsen
Attorney, Agent, or Firm—Luther A. R. Hall

[57] ABSTRACT

A novel process for the preparation of isomelamines of the formula I,

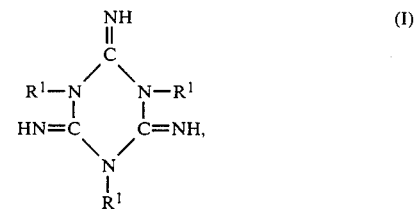

which is characterized in that an N-cyano-N-(ar or cyclo)alkylcarboxylic acid amide or N-cyano-N-allyl-carboxylic acid amide of the formula II or III

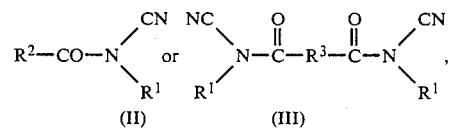

is reacted with aqueous sodium hydroxide solution, potassium hydroxide solution or ammonia solution or a primary aliphatic or cycloaliphatic amine in a solvent or with a primary aliphatic alcohol in the presence of a catalytic amount of a basic compound in a temperature range from −20° C. to 200° C., at least 3 hydroxyl or amino group equivalents being used per 3 carboxylic acid amide group equivalents.

The isomelamines prepared by the process according to the invention are valuable curing agents for epoxide resins.

4 Claims, No Drawings

CURABLE MIXTURES CONTAINING EPOXY RESINS AND ISOMELAMINES

This is a divisional of application Ser. No. 466,454 filed on Feb. 15, 1983, now U.S. Pat. No. 4,499,268.

The present invention relates to a process for the preparation of isomelamines and to the use of these compounds as curing agents for epoxide resins.

The use of isomelamine-modified polyesters is proposed in German Pat. No. 1,951,650 to improve the dyeability of polyester filaments, fibres and yarns. Isomelamines have hitherto only been obtainable by multistage and expensive syntheses, in some cases with low yields. Syntheses for isomelamines are described in, for example, J. appl. Chem., Mar. 6, 1956, 89–93; J. Org. Chem., 25, (1960), 1043–1045 and J. Chem. Soc. (C), 1971, 3827–3829.

We have found that isomelamines can be prepared in a simpler and more economic manner by converting N-cyano-N-alkylcarboxylic acid amides, which are stable compounds, into isomelamines under certain reaction conditions.

The present invention thus relates to a process for the preparation of isomelamines of the formula I

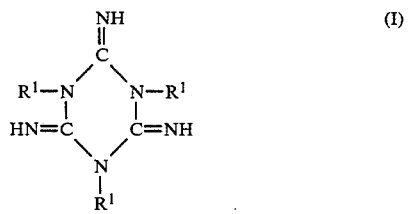

in which each $R^1$ is alkyl having 1 to 8 C atoms, aralkyl having not more than 12 C atoms, allyl or methallyl, which comprises reacting an N-cyano-N-(ar)alkyl- or N-cyano-N-(meth)allylcarboxylic acid amide of the formula II or III

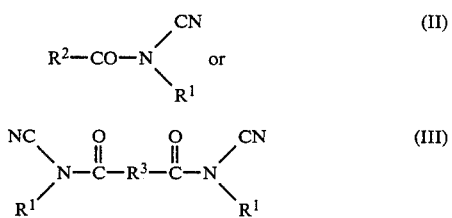

in which each $R^1$ is as defined under formula I, $R^2$ is a hydrogen atom, alkyl having 1 to 16 C atoms, cycloalkyl having 5 to 8 C atoms or aryl having 6 or 10 ring C atoms and $R^3$ is a direct bond or alkylene having 1 to 12 C atoms, with
(a) an aqueous sodium hydroxide potassium hydroxide or ammonia solution or
(b) a primary aliphatic or cycloaliphatic amine in a solvent, or with
(c) a primary aliphatic alcohol in the presence of a catalytic amount of a basic compound,
in each case in a temperature range from $-20°$ C. to $200°$ C., at least 3 hydroxyl or amino group equivalents being used per 3 carboxylic acid amide group equivalents.

The N-cyano-N-(ar)alkyl- or N-cyano-N-(meth)allylcarboxylic acid amide used in the process according to the invention is preferably a compound of the formula II, especially one in which $R^1$ is alkyl having 1 to 4 C atoms or benzyl and $R^2$ is alkyl having 1 to 4 C atoms.

An alkyl group $R^1$ can be straight-chain or branched. Examples of such alkyl groups are methyl, ethyl, n-propyl, isopropyl, n-butyl, sec.-butyl, n-pentyl, 2-pentyl, n-hexyl, n-heptyl, 3-heptyl and n-octyl.

The aralkyl group $R^1$ is preferably 2-phenethyl or benzyl, in particular benzyl.

An alkyl group $R^2$ can be straight-chain or branched and unsubstituted or substituted. Examples of suitable substituents are chlorine and bromine atoms, nitro groups, and alkoxy groups having 1 to 4 C atoms, especially the methoxy group. A cycloalkyl or aryl group $R^2$ may also contain these substituents.

The radical $R^3$, which is derived from an aliphatic dicarboxylic acid, has preferably 1 to 8 C atoms and represents, for example, the corresponding radical of succinic acid, glutaric acid, adipic acid or sebacic acid.

Some of the compounds of the formula II have already been described in the literature, and can advantageously be prepared by reacting 1 mol of an N-cyanocarboxylic acid amide salt of the formula (IV)

in which $R^2$ is as defined under formula II and $M^\oplus$ is an Na or K cation, with 1 mol of an alkylating agent, such as alkyl halide, dimethyl sulfate or diethyl sulfate, in a polar aprotic solvent.

The compounds of the formula III which have not yet been described in the literature can likewise be prepared by reacting 1 mol of a dicarboxylic acid dicyandiamide salt of the formula V

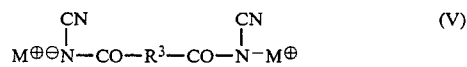

in which $R^3$ is as defined under formula III and $M^\oplus$ is an Na or K cation, with 1 mol of an abovementioned alkylating agent.

In the procedure for the process according to the invention using aqueous sodium hydroxide solution, potassium hydroxide solution or ammonia solution, the concentration of these solutions is not critical. Preferably, 1 to 50% by weight aqueous sodium hydroxide solution or potassium hydroxide solution or 1 to 50% by volume aqueous ammonia solution is used. We have furthermore found that it is advantageous to add a little alcohol, for example ethanol or propanol, to the reaction mixture consisting of a compound of the formula II or III and the aqueous alkali, for better wetting.

Both monoamines and polyamines having at least one primary amino group can be used as the primary aliphatic or cycloaliphatic amines in the process according to the invention.

Examples of suitable amines are methylamine, allylamine, butylamine, iso-butylamine, hexylamine, cyclohexylamine, aminomethylcyclohexane, benzylamine, ethanolamine, 3-propanolamine, ethylenediamine, tetramethylenediamine, hexamethylenediamine, 2,2-dimethyl-1,3-diaminopropane, 2,5-dimethyl-1,5-diaminoheptane, 2,5-dimethyl-1,6-diaminohexane, 2,5-dimethyl-1,7-diaminoheptane, 3,3,5-trimethyl-1,6-diaminohexane, 1,2-bis-(3-aminopropoxy)-ethane, 3-methoxy-1,6- diaminohexane, $H_2N(CH_2)_3O(CH_2)_3NH_2$, $H_2N(CH_2)_3S(CH_2)_3NH_2$, $H_2N-C_2H_4-S-C_2H_4-NH_2$, $H_2N(CH_2)_3N(CH_2)(CH_2)_3NH_2$, N,N'-bis-(3-aminopropyl)-5,5-dimethylhydantoin, 4,4'-diaminodicyclohexylmethane, 3,3'-dimethyl-4,4'-diaminodicyclohexylmethane, 4,4'-diaminodicyclohexyl ether, 4,4'-diaminodicyclohexyl sulfone, 4,4'-diaminodicyclohexylisopropane, 1,4-bis-(aminomethyl)cyclohexane, diethylenetriamine, triethylenetetramine, 3-diethylaminopropylamine, $[(CH_3)_2CHO]_2\text{-}PO(CH_3)_2NH_2$,

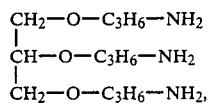

$CH_3-CH_2-C(CH_2-O-C_3H_6-NH_2)_3$,

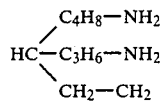

and 1,8-diamino-4-aminomethyloctane.

Primary aliphatic monoamines or diamines are preferably used as the amine.

Both water and organic solvents can be used as the solvent in the reaction of a primary aliphatic or cycloaliphatic amine with a compound of the formula II or III. Examples of suitable organic solvents for this reaction are cycloaliphatic or aromatic hydrocarbons, such as cyclohexane, benzene, toluene and the xylenes; aliphatic or cyclic ethers, such as diethyl ether, dioxane and tetrahydrofuran; chlorinated aliphatic hydrocarbons, such as methylene chloride, chloroform, carbon tetrachloride, trichloroethylene and dichloroethane; ethylene glycol dimethyl ether and ethylene glycol diethyl ether; alkanols, such as methanol, ethanol, n-propanol, isopropanol and butanol; aliphatic ketones, such as acetone; cyclic amides, such as N-methylpyrrolidone; N,N-dialkylamides of lower aliphatic monocarboxylic acids, such as N,N-dimethylformamide and N,N-dimethylacetamide; dialkylsulfoxides, such as di-methyl- and diethyl-sulfoxide; hexamethylphosphoric acid triamide and sulfolane; alkylnitriles having 2-5 C atoms, such as acetonitrile, propionitrile and butyronitrile; and cyclic amines, such as pyridine and its derivatives.

The concentrations of the compounds of the formula II or III and the primary aliphatic or cycloaliphatic amine in the solvent can vary within wide limits, and are advantageously between 10 and 50% by weight, preferably between 20 and 40% by weight.

Both monools and polyols can be used in the procedure of the process according to the invention using a primary aliphatic alcohol. Examples of suitable polyols are di-, tri- and tetra-ols, which canbe straight-chain or branched and unsaturated or saturated, and may be interrupted by ether-oxygen atoms or contain an aliphatic radical substituted by halogen atoms, alkoxy or phenoxy. Examples of such compounds are methanol, ethanol, propanol, ethylene glycol, propane-1,3-diol, hexane-1,6-diol, neopentylglycol, 2-ethylhexane-1,3-diol, butane-1,4-diol, diethylene glycol, dipropylene glycol, 1,1,1-trimethylolethane, 1,1,1-trimethylolpropane, glycerol, hexane-1,2,6-triol and pentaerythritol.

An aliphatic monool or diol is preferably used as the alcohol.

In principle, suitable catalysts are all the basic compounds, for example sodium hydroxide solution, potassium hydroxide solution, ammonia, primary, secondary or tertiary amines, such as methylamine, butylamine, benzylamine, diethylamine, tributylamine or triethylamine, quaternary ammonium bases, such as benzyltrimethylammonium hydroxide, heterocyclic bases, such as pyridine, quinoline, N-methylpyrrolidone, imidazole and derivatives thereof, and alkali metal alcoholates, such as sodium methylate.

The process according to the invention can be carried out within a broad temperature range, preferably in the temperature range from 0° to 120° C. As mentioned above, isomelamines are modifying agents for polyesters. Moreover, hydrolysis of trialkylisomelamines gives the corresponding trialkylcyanuric acids.

We have also found that the isomelamines prepared according to the invention are useful curing agents for epoxide resins. The present invention thus also relates to the use of isomelamines of the formula I in curable mixtures consisting of epoxide resins and the isomelamines.

The amount of isomelamine used as the curing agent in these curable mixtures is usually calculated such that 0.75 to 1.25 NH equivalents of isomelamine are present per epoxide equivalent. Equivalent amounts of the isomelamine and the epoxide resin component are preferably used.

Epoxide resins in which groups of the formula IV

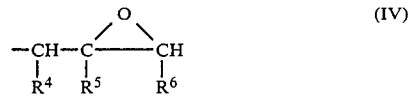

in which either $R^4$ and $R^6$ are each hydrogen atoms, in which case $R^5$ is a hydrogen atom or a methyl group, or $R^4$ and $R^5$ together are $-CH_2CH_2-$, in which case $R^5$ is a hydrogen atom, are bonded directly to oxygen, nitrogen or sulfur atoms are preferably used for the curable mixtures.

Examples of such resins are polyglycidyl and poly(β-methylglycidyl) esters, which can be obtained by reacting a compound containing two or more carboxyl groups per molecule with epichlorohydrin, glycerol dichlorohydrin or β-methylepichlorohydrin in the presence of an alkali. Such polyglycidyl esters can be derived from aliphatic polycarboxylic acids, for example oxalic acid, succinic acid, glutaric acid, adipic acid, sebacic acid or dimerised or trimerised linoleic acid, from cycloaliphatic polycarboxylic acids, such as tetrahydrophthalic acid, 4-methyltetrahydrophthalic acid, hexahydrophthalic acid or 4-methylhexahydrophthalic acid, and from aromatic polycarboxylic acids, such as phthalic acid, isophthalic acid or terephthalic acid.

Other examples are polyglycidyl and poly(β-methylglycidyl) ethers, which can be obtained by reacting a compound containing at least two free alcoholic and/or phenolic hydroxyl groups per molecule with the corresponding epichlorohydrin under alkaline conditions, or in the presence of an acidic catalyst with subsequent treatment with an alkali. These ethers can be prepared with poly-(epichlorohydrin) from acyclic alcohols, such as ethylene glycol, diethylene glycol and higher poly-(oxyethylene) glycols, propane-1,2-diol and poly- (oxypropylene) glycols, propane-1,3-diol, butane-1,4-diol, hexane-2,4,6-triol, glycerol, 1,1,1-trimethylolpropane, pentaerythritol or sorbitol, from cycloaliphatic alcohols, such as resorcitol, quinitol, bis-(4-hydroxycyclohexyl)-methane, 2,2-bis-(4-hydroxycyclohexyl)-propane or 1,1-bis-(hydroxymethyl)-cyclohex-3-ene, and from alcohols with aromatic nuclei, such as N,N-bis-(2-hydroxyethyl)-aniline or p,p'-bis-(2-hydroxyethylamino)-diphenylmethane. Further suitable epoxide resins are those obtained from mononuclear phenols, such as resorcinol and hydroquinone, and polynuclear phenols, such as bis-(4-hydroxyphenyl)-methane, 4,4'-dihydroxydiphenyl, bis-(4-hydroxyphenyl) sulfone, 1,1,2,2-tetrakis-(4-hydroxyphenyl)-ethane, 2,2-bis-(4-hydroxyphenyl)-propane (bisphenol A) or 2,2-bis-(3,5-dibromo-4-hydroxyphenyl)-propane, and novolaks which are formed from aldehydes, such as formaldehyde, acetaldehyde, chloral or furfuraldehyde, with phenols, such as phenol itself or phenol which is ring-substituted by chlorine atoms or alkyl groups having in each case not more than nine carbon atoms, such as 4-chlorophenol, 2-methylphenol or 4-tert.-butylphenol.

Examples of other suitable poly-(N-glycidyl) compounds include those which are prepared by dehydrochlorination of the reaction products of epichlorohydrin with amines containing at least two amino-hydrogen atoms, such as aniline, n-butylamine, bis-(4-aminophenyl)-methane or bis-(4-methylaminophenyl)-methane, and triglycidyl isocyanurate or N,N'-diglycidyl derivatives of cyclic alkyleneureas, such as ethyleneurea or 1,3-propyleneurea, or hydantoins, such as 5,5-dimethylhydantoin.

Examples of epoxide resins carrying groups of the formula IV in which $R^4$ and $R^6$ together are a —$CH_2CH_2$— group are bis-(2,3-epoxycyclopentyl) ether, 2,3-epoxycyclopentyl-glycidyl ether and 1,2-bis-(2,3-epoxycyclopentyloxy)-ethane.

Epoxide resins in which some or all of the epoxide groups are non-terminal, such as vinylcyclohexene dioxide, limonene dioxide, dicyclopentadiene dioxide, the 3,4-epoxycyclohexylmethyl ester of 3',4'-epoxycyclohexanecarboxylic acid and its 6,6'-dimethyl derivative, the bis-(3,4-epoxycyclohexanecarboxylic acid ester) of ethylene glycol, bis-(3,4-epoxy-6-methylcyclohexyl) adipate and 3-(3,4-epoxycyclohexyl)-8,9-epoxy-2,4-dioxaspiro[5,5]undecane can also be used.

The curable mixtures according to the invention can furthermore also contain plasticising agents, such as dibutyl phthalate, dioctyl phthalate or tricresyl phosphate, or additives, such as fillers, reinforcing agents, colorants, flow control agents, flame-retarding substances and mould release agents. Examples of suitable extenders, fillers and reinforcing agents are asbestos, asphalt, bitumen, glass fibres, textile fibres, carbon or boron fibres, mica, aluminas, gypsum, titanium dioxide, chalk, quartz flour, cellulose, kaolin, ground dolomite, wollastonite, silica having a high specific surface area (obtainable under the tradename "Aerosil"), aluminas modified by long-chain amines (obtainable under the tradename "Bentone"), powdered poly-(vinyl chloride), polyolefin or aminoplast, and metal powders, such as aluminium powder or iron powder. Flame retardants, such as antimony trioxide, can also be added to the curable mixtures.

In the examples which follow and which illustrate the invention in more detail, parts are by weight, unless otherwise indicated.

EXAMPLES 1–14

1,3,5-Trimethylisomelamine

1. A solution of 3.0 g of KOH (0.0536 mol) in 20 ml of $H_2O$ is added to 5.19 g (0.0529 mol) of N-cyano-N-methylacetamide, 1 ml of ethanol being added for better wetting. The mixture undergoes an exothermic reaction, and a clear solution is formed. The solution is heated briefly to the boiling point; on cooling, the product crystallises out. The mixture is cooled overnight in a refrigerator and the product is filtered off with suction, washed with cold water and dried at 70° C. in a vacuum drying cabinet. Yield: 2.16 g (72.8% of theory), melting point: 175°–177° C. (literature: 178° C. [1][2][3]). If the $H_2O$-free compound thus dried is left to stand open in the air for 6 days, it absorbs 3 mols of water of crystallisation, and melts, releasing this water, when a sample is brought to 150° C. in a melting block.

(1) R. Kitawaki, J. Org. Chem. 25, 1043 (1960)
(2) A. W. Hofmann, Chem. Ber. 3, 264
(3) A. W. Hofmann, Chem. Ber. 18, 2784 (1885)

Analysis for $C_6H_{12}N_6 \cdot 3H_2O$: calculated: $H_2O = 24.32\%$, found: $H_2O = 23.83\%$.

The $^{13}$C-NMR spectrum confirms the structure for 1,3,5-trimethylisomelamine: 148.4 ppm (ring C; septet); 31.5 ppm ($CH_3$; quartet).

2. 2.52 g (0.030 mol) of N-cyano-N-methylformamide are dissolved in 5 ml of ethanol, 1.85 g (0.033 mol) of KOH dissolved in 5 ml of $H_2O$ are added and the mixture is heated briefly to the boiling point. On cooling, a large amount of product crystallises out. The mixture is diluted with a further 10 ml of $H_2O$, and the product is dissolved again by heating and left to crystallise out at room temperature. Filtration with suction, washing with $H_2O$ and drying at 50° C. in vacuo gives 0.92 g (54.7% of theory) of product of melting point 180° C. Concentration of the filtrate gives a further 0.14 g (8.3%) of melting point 179°–180° C.

3. 3.20 g (0.020 mol) of N-cyano-N-methylbenzamide are dissolved in 5 ml of ethanol, and a solution of 1.23 g of KOH (0.022 mol) in 3 ml of $H_2O$ is added. The mixture is heated briefly to the boiling point; on cooling, the product crystallises out. The mixture is cooled in a refrigerator and the product is filtered off with suction, washed with cold 40% ethanol and dried at 60° C. in vacuo. Yield: 0.5 g (48.2% of theory), melting point: 177°–179° C.

4. 4.76 g (0.020 mol) of lauric acid N-cyano-N-methylamide are dissolved in 10 ml of warm ethanol, and a solution of 1.23 g (0.022 mol) of KOH in 2 ml of $H_2O$ is added. The mixture is heated briefly to the boiling point and is then cooled in a refrigerator. Filtration with suction, washing with cold ethanol and drying at 60° C. in vacuo gives 0.44 g (39% of theory) of product of melting point 180° C.

5. 13.33 g (0.060 mol) of adipic acid N,N'-dicyano-N,N'-dimethyldiamide are stirred overnight with 1 ml of triethylamine in 20 ml (0.268 mol) of n-propanol in an oil bath of 100° C. On cooling, the product crystallises out and, after addition of 20 ml of acetone, is filtered off with suction, washed with acetone and then dried. Yield: 2.91 g (86.6% of theory); melting point: 179° C. Concentration of the filtrate gives further solid product, mixed with a little of some resinous constituents. The latter dissolves in acetone. The mixture is filtered off with suction, washed with acetone and dried to give a further 0.89 g of impure product. Both fractions are recrystallised together from 10 times the amount of H₂O (37 ml) and the product is filtered off cold, with suction, washed with cold H₂O and dried at 60° C. in vacuo. Yield: 3.13 g (93.0% of theory); melting point: 178°–179° C.

6. 2.94 g (0.03 mol) of N-cyano-N-methylacetamide are refluxed in 12 ml of tetrahydrofuran with 3.21 g (0.03 mol) of benzylamine for 8 hours. The product crystallises out on cooling, and is filtered off with suction, washed with tetrahydrofuran and dried at 80° C. in vacuo. Yield: 0.52 g; melting point 173°–176° C. The filtrate is concentrated and the residue is recrystallised from a mixture of 15 ml of H₂O and 3 ml of ethanol. A further 0.56 g of product of melting point 176°–178° C. is obtained. Total yield: 1.08 g (68.7% of theory).

7. 3 ml of 25% aqueous ammonia (0.044 mol) are added to 2.52 g (0.03 mol) of N-cyano-N-methylacetamide in 7 ml of H₂O. The product dissolves under intrinsic warming. The mixture is heated briefly to the boiling point, after which the product crystallises out on cooling. The mixture is filtered with suction, washed with cold water and dried at 60° C. in vacuo to give 0.94 g (55.9%) of trimethylisomelamine.

8. 4.90 g (0.05 mol) of N-cyano-N-methylacetamide are dissolved in 15 ml (0.2 mol) of n-propanol, 0.3 ml of triethylamine is added and the mixture is immersed in an oil bath of 85° C. overnight. On cooling, the product crystallises out. Filtration with suction, washing with n-propanol and drying at 70° C. in vacuo gives 1.44 g of product of melting point 170°–173° C. Concentration of the filtrate, recrystallisation of the residue from 5 ml of water and drying at 60° C. in vacuo gives a further 0.87 g of product of melting point 170°–173° C. Total yield of crude compound: 2.31 g (82.4%).

9. A solution of 4.87 g (0.087 mol) of KOH in 10 ml of H₂O is added to 5.67 g (0.0579 mol) of N-cyano-N-methylacetamide and the mixture is heated. After 2 minutes, the mixture is allowed to cool, whereupon the product crystallises out. After filtration with suction, washing with H₂O and drying at 60° C. in vacuo, 1.42 g (43.7% of theory) of 1,3,5-trimethylisomelamine are obtained.

10. 2.94 g (0.030 mol) of N-cyano-N-methylacetamide are refluxed in 7.2 g (0.12 mol) of n-propanol and 0.22 g of diethylamine for 21 hours. The clear solution crystallises on cooling. Filtration with suction, washing with n-propanol and drying at 60° C. in vacuo gives 0.68 g (40.4%) of product of melting point 178°–180° C. A further 0.45 g (26.8% of theory) of product of melting point 175°–179° C. can be isolated from the filtrate by concentration.

11. 2.94 g (0.030 mol) of N-cyano-N-methylacetamide are dissolved in 15 ml (0.164 mol) of n-butanol with 0.64 g of 1-dimethylaminododecane and the solution is immersed in a bath of 100° C. for 17 hours. On cooling, the product crystallises out, and is filtered off with suction, washed and dried. Yield: 0.59 g. Concentration of the mother liquor gives a further 0.36 g. The total yield is thus 0.95 g (56.5% of theory); melting point: 176°–180° C.

12. 2.95 g (0.030 mol) of N-cyano-N-methylacetamide are dissolved with 0.35 g of N,N,N',N'-tetramethylethylenediamine in 20 ml (0.105 mol) of decanol under the influence of heat, and the solution is immersed in a bath of 100° C. for 18 hours. The product crystallises on cooling, and the educt can no longer be detected in the liquid phase by gas chromatography. Isopropanol is added and the product is filtered off with suction, washed with isopropanol and dried at 60° C. in vacuo. Yield: 0.50 g; melting point: 180°–181° C. The filtrate is concentrated and, after excess n-decanol has been completely removed by vacuum distillation, 5 ml of H₂O and 2.5 ml of ethanol are added. On heating, a clear solution is formed, from which a further 0.37 g of product of melting point 176°–179° C. crystallises out. Total yield: 0.87 g (51.7% of theory).

13. 2.94 g (0.030 mol) of N-cyano-N-methylacetamide are refluxed overnight with 5.59 g (0.090 mol) of ethylene glycol and 0.30 g (0.003 mol) of triethylamine in 5 ml of tetrahydrofuran. All the constituents having boiling points of up to 140° C. under 26 mbar are then removed, and the residue is recrystallised from 12 ml of H₂O. Yield: 0.89 g (52.9% of theory); melting point: 179°–181° C.

14. 2.94 g (0.030 mol) of N-cyano-N-methylacetamide are boiled with 2.34 g (0.016 mol) of triethylenetetramine in 15 ml of tetrahydrofuran for 5 hours; on cooling, 0.70 g of product of melting point 179°–181° C. crystallises out. A further 0.48 g of substance of melting point 178°–181° C. is obtained by concentration of the mother liquor; the total yield is thus 1.18 g (70.2% of theory).

EXAMPLES 15 AND 16

1,3,5-Triethylisomelamine 15. 2.24 g (0.02 mol) of N-cyano-N-ethylacetamide are dissolved in a mixture of 2 ml of ethanol and 3 ml of H₂O at room temperature, and a solution of 1.3 g (0.0232 mol) of KOH in 3 ml of H₂O is added. An oil separates out, and dissolves again as a result of the exothermic reaction. The mixture is cooled in a refrigerator overnight and the product is filtered off with suction, washed with cold water and dried at 60° C. in vacuo. Yield: 0.89 g (63.6% of theory); melting point: 91°–92° C. (literature: [3] 92° C.). Concentration of the filtrate gives a further 0.24 g (17.1%) of melting point 89°–91° C. Both fractions are recrystallised again together from 7 ml of H₂O, and after the mixture has been cooled in a refrigerator for 6 hours, the product is filtered off with suction, washed with cold water and dried at 40° C. in vacuo. Yield: 1.10 g (78.6% of theory); melting point: 91°–92° C. When the product is left to stand open in the air, it absorbs no water of crystallisation; H₂O analysis: content <0.3% of H₂O. The $^{13}$C-NMR spectrum confirms the structure: 146.6 ppm (ring C; quintet); 39.3 ppm (CH₂); 11.9 ppm (CH₃).

16. 4.49 g (0.04 mol) of N-cyano-N-ethylacetamide are immersed in an oil bath at 110° C. with 15 ml (0.2 mol) of n-propanol and 0.3 ml of triethylamine for 24 hours, after which the educt can no longer be detected by gas chromatography. The mixture is concentrated on a rotary evaporator to give an oil, which solidifies as crystals at room temperature. Recrystallisation from 6 ml of H₂O, filtration with suction, washing with cold H₂O and drying in vacuo at 35° C. gives 1.28 g (45% of theory) of substance of melting point 90°–91° C.

EXAMPLE 17

1,3,5-Triallylisomelamine

A solution of 3.4 g (0.0607 mol) of KOH in 10 ml of H₂O is added to 7.44 g (0.06 mol) of N-cyano-N-allylacetamide. After 6 ml of ethanol have been added, the mixture becomes homogeneous, and reacts exothermically. After a short time, an oil separates out, and can be dissolved by addition of 3 ml of ethanol and brief boiling. After the mixture has been cooled, it is diluted with 10 ml of H₂O and extracted with 3 portions of chloroform (20, 10 and 10 ml). Concentration of the extracts on a rotary evaporator gives 4.77 g of a colourless oil, which, for purification, is distilled in a bulb tube oven. 3.54 g (71.9% of theory) of distillate of boiling point ~105°–115° C. under 0.026 mbar, which solidifies as crystals at room temperature and, according to gas chromatography, is over 97% pure, are obtained.

| Analysis $C_{12}H_{18}N_6$ (M = 246.32): | | | | | |
|---|---|---|---|---|---|
| calculated: | C | 58.52% | found: | C | 58.32% |
| | H | 7.37% | | H | 7.34% |
| | N | 34.12% | | N | 34.57% |

EXAMPLE 18

1,3,5-Tri-n-butylisomelamine 12.60 g (0.09 mol) of N-cyano-N-butylacetamide are refluxed with 13.4 g (0.1035 mol) of diethylaminopropylamine in 25 ml of tetrahydrofuran for 2 hours, after which, according to investigation by gas chromatography, the educt has completely reacted to give 3-diethylaminopropylacetamide, tri-n-butylisomelamine and another component, which probably consists of butyl cyanamide. The mixture is concentrated on a rotary evaporator, and the oil which remains is left to stand at room temperature and the reaction which subsequently takes place is monitored by gas chromatography. After 5 days, the unknown component, which probably consists of butyl cyanamide, has largely reacted and has formed tributylisomelamine by trimerisation. The mixture is distilled in a bulb tube oven, first under 23.4 mbar and at a maximum temperature of 125° C. and then under 0.156 mbar and at a maximum temperature of 180° C. 6 fractions totalling 24.4 g are thereby obtained, analysis of which by gas chromatography gives a yield of 74.7% of tributylisomelamine and 96.7% of 3-diethylaminopropylacetamide. An analysis sample of tributylisomelamine, which is liquid at room temperature, can be isolated by renewed distillation of the fractions obtained under the high vacuum.

| Analysis $C_{15}H_{30}N_6$ (M = 294.45) | | | | | |
|---|---|---|---|---|---|
| calculated: | C | 61.19% | found: | C | 61.15% |
| | H | 10.27% | | H | 10.12% |
| | N | 28.54% | | N | 28.69% |

¹³C-NMR spectrum (ppm): 147.2 (ring C); 44.1 (NCH₂); 28.7 (CH₂); 20.2 (CH₂); 13.8 (CH₃).

The dipicrate of melting point 179°–181° C. is obtained from ethanol with picric acid.

| Analysis $C_{15}H_{30}N_6 \cdot 2C_6H_3N_3O_7$ (M = 752.66) | | | | | |
|---|---|---|---|---|---|
| calculated: | C | 43.09% | found: | C | 42.94% |
| | H | 4.82% | | H | 4.80% |
| | N | 22.33% | | N | 22.43% |
| | O | 29.76% | | O | 30.04%. |

EXAMPLE 19

1,3,5-Tri-isobutylisomelamine 3.25 g (0.0232 mol) of N-cyano-N-isobutylacetamide are boiled with 10 ml of ethanol and 1.55 g (0.0277 mol) of KOH, dissolved in 10 ml of H₂O, for 60 minutes. The mixture is then concentrated on a rotary evaporator, 10 ml of H₂O are added and the mixture is extracted with methylene chloride. After removal of the solvent, 1.40 g of crude product are obtained, which solidifies as crystals at room temperature. The product is distilled in a bulb tube oven at 80°–110° C. and under $1.3 \cdot 10^{-3}$ mbar to give 0.78 g of an oil which solidifies at room temperature. Recrystallisation from a mixture of n-hexane and benzene gives 0.30 g of pure triisobutylmelamine of melting point 91°–93° C.

| Analysis $C_{15}H_{30}N_6$ (M = 294.45) | | | | | |
|---|---|---|---|---|---|
| calculated: | C | 61.19% | found: | C | 60.97% |
| | H | 10.27% | | H | 10.12% |
| | N | 28.54% | | N | 28.48% |

¹³C-NMR spectrum (ppm): 148.2 (ring C); 51.0 (NCH₂); 26.8 (CH); 20.2 (CH₃).

EXAMPLE 20

1,3,5-Tribenzylisomelamine 52.2 g (0.30 mol) of N-cyano-N-benzylacetamide are refluxed in 150 ml of tetrahydrofuran with 44.9 g (0.3448 mol) of 3-diethylaminopropylamine for 2½ hours. The mixture is concentrated on a rotary evaporator and the residue of 101 g is recrystallised from 300 ml of cyclohexane to give 28.2 g of product of melting point 124°–126° C. Concentration of the mother liquor and recrystallisation of the residue from 300 ml of n-hexane gives a further 4.60 g of product of melting point 119°–121° C. The total yield is thus 32.8 g (82.8% of theory). For further purification, the product is recrystallised again from a mixture of 100 ml of cyclohexane and 66 ml of toluene. Yield: 28.7 g; melting point: 129°–129.5° C. (literature [4]: 129°–130° C.).

(4) L. Birkofer, Chem. Ber. 75, 429.

USE EXAMPLES I–IV

Liquid bisphenol A diglycidyl ether with an epoxide content of 5.35 equivalents/kg and a trialkylisomelamine are mixed at room temperature on a triple-roll mill in ratios such that one epoxide group equivalent is present for each NH equivalent of the isomelamine. These suspensions are then further investigated.

(a) Glass transition temperature (GTT):

4 g of the suspension are introduced into a thin-walled aluminium crucible and are cured. The GTT values of samples of the cured material are determined by means of differential thermal analysis ("TA 2000" apparatus from Mettler, Greifensee, CH).

(b) Tensile strength:

A small amount of the suspension is applied to the ends of test strips of Anticorodal sheet (aluminium alloy), which has first been roughened by abrasion and degreased with solvents. The dimensions of the strips are 170×25×15 mm. The strips are allowed to overlap 12 mm, are fixed with a clamp and are cured. The tensile shear strength according to DIN 53,183 is then determined.

The values are summarised in the table which follows.

|  | Use Examples | | | |
| --- | --- | --- | --- | --- |
|  | I | II | III | IV |
| NH ‖ RN NR HN N NH R | R = —CH₃ 30.5 g | R = —C₂H₅ 38.2 g | R = CH₂CH=CH₂ 44.7 g | R = —CH₂C₆H₅ 71.9 g |
| Epoxide resin | 100 g | 100 g | 100 g | 100 g |
| Curing conditions |  |  | 6 hours at 180° C. |  |
| GTT | 95° C. | 80° C. | 93° C. | 77° C. |
| Tensile shear strength [N/mmu 2] | 9.9 | 19.0 | 16.5 | 9.4 |

What is claimed is:

1. A curable mixture which comprises
   (a) an epoxy resin having more than one epoxy group in the molecule, and
   (b) an isomelamine of formula I

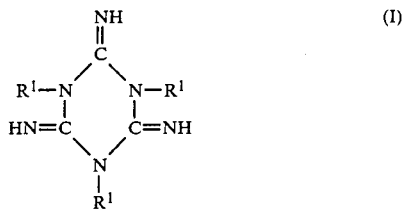

in which each $R^1$ is alkyl having 1 to 8 C atoms, aralkyl having not more than 12 C atoms, allyl or methallyl, in which there are 0.75 to 1.25 NH equivalents per epoxide equivalent.

2. A mixture according to claim 1 where in the isomelamine of formula I $R^1$ is alkyl having 1 to 4 C atoms, allyl or benzyl.

3. A mixture according to claim 1 in which the isomelamine of formula I is 1,3,5-trimethylisomelamine, 1,3,5-triethylisomelamine, 1,3,5-triallylisomelamine or 1,3,5-tribenzylisomelamine.

4. A mixture according to claim 1 in which the epoxy resin is a liquid diglycidyl ether of bisphenol A.

* * * * *